(12) United States Patent
Bonnert et al.

(10) Patent No.: US 8,507,544 B2
(45) Date of Patent: Aug. 13, 2013

(54) BI-ARYL AMIDE COMPOUNDS AS CRTH2 RECEPTOR MODULATORS

(75) Inventors: Roger Victor Bonnert, Loughborough (GB); Timothy Jon Luker, Loughborough (GB); Anil Patel, Loughborough (GB); Aaron Rigby, Loughborough (GB)

(73) Assignee: Astrazeneca AB, Sodertalje (SE)

( * ) Notice: Subject to any disclaimer, the term of this patent is extended or adjusted under 35 U.S.C. 154(b) by 608 days.

(21) Appl. No.: 12/167,513

(22) Filed: Jul. 3, 2008

(65) Prior Publication Data

US 2009/0012151 A1    Jan. 8, 2009

Related U.S. Application Data

(60) Provisional application No. 60/948,012, filed on Jul. 5, 2007.

(51) Int. Cl.
*A61K 31/40*    (2006.01)
*C07D 295/00*    (2006.01)

(52) U.S. Cl.
USPC ............................................ 514/423; 548/539

(58) Field of Classification Search
USPC ........................................ 514/423; 548/539
See application file for complete search history.

(56) References Cited

U.S. PATENT DOCUMENTS

| | | |
|---|---|---|
| 3,278,524 A | 10/1966 | Johnson et al. |
| 3,920,846 A | 11/1975 | Hanauye et al. |
| 4,670,566 A | 6/1987 | Walsh |
| 5,006,542 A | 4/1991 | Hall et al. |
| 5,145,790 A | 9/1992 | Mattingly et al. |
| 5,411,972 A | 5/1995 | Komoto et al. |
| 5,413,891 A | 5/1995 | Matsuura et al. |

(Continued)

FOREIGN PATENT DOCUMENTS

| | | |
|---|---|---|
| CH | 432119 | 9/1967 |
| EP | 0114734 | 8/1984 |

(Continued)

OTHER PUBLICATIONS

Vippagunta et al, "Crystalline Solids", Advanced Drug Delivery Reviews, vol. 48, pp. 3-26 (2001).*

(Continued)

*Primary Examiner* — Yong Chu
*Assistant Examiner* — Valerie Rodriguez-Garcia

(57) ABSTRACT

The present invention relates to (2S)-2-({3'-Chloro-4'-[(2,2-dimethylpyrrolidin-1-yl) carbonyl]-5-fluorobiphenyl-2-yl}oxy)propanoic acid and (2R)-2-({3'-chloro-4'-[(2,2-dimethylpyrrolidin-1-yl) carbonyl]-5-fluorobiphenyl-2-yl}oxy) propanoic acid of formula (I), and crystalline forms and pharmaceutically acceptable salts thereof useful as pharmaceuticals.

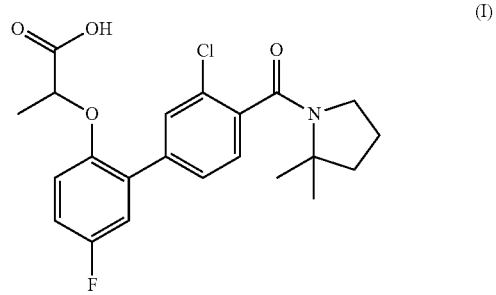

(I)

17 Claims, 3 Drawing Sheets

XRPD for Example 2 Polymorph A

(56) References Cited

U.S. PATENT DOCUMENTS

| | | | |
|---|---|---|---|
| 5,532,371 | A | 7/1996 | Komoto et al. |
| 5,703,099 | A | 12/1997 | Hamanaka et al. |
| 6,150,413 | A | 11/2000 | Bernardon et al. |
| 6,376,546 | B1 | 4/2002 | Shoda et al. |
| 6,417,212 | B1 | 7/2002 | Brooks et al. |
| 7,056,942 | B2 | 6/2006 | Hildesheim et al. |
| 7,067,507 | B2 | 6/2006 | Pullet et al. |
| 7,737,135 | B2 | 6/2010 | Luker et al. |
| 2004/0029933 | A1 | 2/2004 | Zhao et al. |
| 2004/0097555 | A1 | 5/2004 | Ohkawa et al. |
| 2004/0220237 | A1 | 11/2004 | Fu et al. |
| 2005/0239881 | A1 | 10/2005 | Dunn et al. |
| 2006/0211765 | A1 | 9/2006 | Pairaudeau et al. |
| 2006/0264435 | A1 | 11/2006 | Bonnert et al. |
| 2006/0293352 | A1 | 12/2006 | Bonnert et al. |
| 2007/0249686 | A1 | 10/2007 | Bonnert et al. |
| 2008/0114002 | A1 | 5/2008 | Bonnert et al. |
| 2008/0132480 | A1 | 6/2008 | Luker et al. |
| 2008/0255150 | A1 | 10/2008 | Luker |
| 2008/0293775 | A1 | 11/2008 | Bonnert et al. |
| 2009/0012151 | A1 | 1/2009 | Bonnert et al. |
| 2009/0036535 | A1 | 2/2009 | Luker et al. |
| 2009/0149448 | A1 | 6/2009 | Alcaraz et al. |
| 2009/0192163 | A1 | 7/2009 | Luker et al. |

FOREIGN PATENT DOCUMENTS

| | | |
|---|---|---|
| EP | 0540165 | 5/1993 |
| EP | 0622690 | 11/1994 |
| EP | 0839808 | 5/1998 |
| EP | 1012142 | 6/2000 |
| EP | 1170594 | 1/2002 |
| EP | 1211513 | 6/2002 |
| EP | 1471057 | 10/2004 |
| GB | 1 356 834 | 6/1974 |
| GB | 1 464 977 | 2/1977 |
| GB | 1 469 687 | 4/1977 |
| GB | 2 031 408 | 4/1980 |
| GB | 2 041 363 | 9/1980 |
| GB | 1 585 963 | 3/1981 |
| JP | 07140725 | 6/1995 |
| JP | 2003-508389 | 3/2003 |
| WO | WO 93/12086 | 6/1993 |
| WO | WO 97/08126 | 3/1997 |
| WO | WO 99/11605 | 3/1999 |
| WO | WO 99/11627 | 3/1999 |
| WO | WO 01/16120 | 3/2001 |
| WO | WO 01/60807 | 8/2001 |
| WO | WO 01/81312 | 11/2001 |
| WO | WO 01/92224 | 12/2001 |
| WO | WO 03/064387 | 8/2003 |
| WO | WO 03/066047 | 8/2003 |
| WO | WO 03/068744 | 8/2003 |
| WO | WO 03/101961 | 12/2003 |
| WO | WO 2004/007451 | 1/2004 |
| WO | WO 2004/048314 | 6/2004 |
| WO | WO 2004/058164 | 7/2004 |
| WO | WO 2004/089884 | 10/2004 |
| WO | WO2004/089885 | 10/2004 |
| WO | WO 2004/094386 | 11/2004 |
| WO | WO 2004/096777 | 11/2004 |
| WO | WO 2005/018529 | 3/2005 |
| WO | WO 2005/044260 | 5/2005 |
| WO | WO 2005/105727 | 11/2005 |
| WO | WO 2005/115382 | 12/2005 |
| WO | WO 2006/005909 | 1/2006 |
| WO | WO 2006/021759 * | 3/2006 |
| WO | WO2006/021759 | 3/2006 |
| WO | WO 2006/037982 | 4/2006 |
| WO | WO 2006/056752 | 6/2006 |
| WO | WO 2006/125596 | 11/2006 |
| WO | WO 2007/039736 | 4/2007 |
| WO | WO 2007/039741 | 4/2007 |
| WO | WO 2007/052023 | 5/2007 |
| WO | WO 2007/068894 | 6/2007 |

OTHER PUBLICATIONS

Gavezzotti, "Are Crystal Structures Predictable?", Accounts of Chemical Research, vol. 27, pp. 309-314 (1994).*
Amin et al., "The Fries Reaction: Part VI—the rearrangement of aryl p-toluene-sulphonates & a convenient method for synthesis of ydroxyl-diarylsulphones", Journal of Scientific Industrial Research, vol. 13B, 1954, pp. 181-183.
Atkinson et al., "Substituted (2-Phenoxyphenyl)acetic Acids with Antiinflammatory Activity", J. Med. Chem., vol. 26, 1983, pp. 1353-1360.
Baliah et al., "Fries rearrangement of the benzenesulphonates of xylenols", Recueil des Travaux Chimiques des Pays-Bas, vol. 80, 1961, pp. 139-148.
Bartl et al., "Thioxanthene Derivatives of Pharmacological Interest: 1,2,4-Trichloro and 2,4,5,6-Tetrachloro Derivatives of 9-(3-Dimethylaminopropylidene)Thioxanthene", Collection Czechoslov. Chem. Commun., vol. 49, 1984, pp. 2295-2308.
Brown et al., "Some Chlorinated Hydroxyphenoxyacetic Acids", Journal of the Chemical Society, 1955, pp. 3681-3687.
Budavari, S., "The merck Index, 13$^{th}$ edition", p. 3106, monograph 3108, XP-002347170, 2001.
Cavill et al., "The chemistry of plant-growth regulators. Part I. 2:4-dichloro-6-hydroxyphenoxyacetic acid and related compounds", Journal of the Chemical Society, 1954, pp. 565-569.
Cecil Textbook of Medicine, 20$^{th}$ ed. (1996), vol. 2, pp. 1992-1996.
Cecil Textbook of Medicine, 20$^{th}$ ed. (1996), vol. 2, pp. 2050-2057.
Chiu et al., "Derivation and Properties of Recombinant Fab Antibodies to Coplanar Polychlorinated Biphenyls", J. Agric. Food Chem. 48:2614-2624 (2000).
Clemo et al., "Strychnine and brucine. Part II", Journal of the Chemical Society, vol. 125, 1924, pp. 1751-1804, XP008053173.
Cocco et al., "Annulation of functionalized hexadienones as an efficient regioselective approach to N-Aryl-2-(trifluoromethyl)-4-pyridinamines", Tetrahedron Letters, vol. 40, No. 23, 1999, pp. 4407-4410.
Dalal et al., "Synthetic insecticides. I. Synthesis of α, α-bis(aryl)-β, β, δ-trichlorobutanes", STN Accession No. 1950:35789, Document No. 44:35789, Abstract of Journal of the Indian Chemical Society 26:549-52 (1949).
FDA mulls drug to slow late-stage Alzheimer's [online], [retrieved Sep. 24, 2003]. Retrieved from the Internet, URL; http://www.cnn.com/2003/HEALTH/conditions/09/24/alzheimers.drug.ap/index.html>.
Gallo et al., "Spirodioxolanonarenones. II. Synthesis of a halogenated 1,4-dioxaspiro[4,5]deca-7,9-diene-2,6-dione", Journal of Chemistry, vol. 30, No. 5, 1965, pp. 1657-1658.
Gaunt et al., "Metabolism of 4-chloro-2-methylphenoxyacetate by a soil pseudomonad", Biochem. J., vol. 122, 1971, pp. 519-526.
Golub et al., "Molecular Classification of Cancer: Class Discovery and Class Prediction by Gene Expression Monitoring", Science 286:531-537 (1999).
Hazeldine et al., "Design, Synthesis and Biological Evaluation of Analogues of the Antitumor Agent, 2-{4-[(7-Chloro-2-quinoxalinyl)oxy]phenoxy}propionic Acid (XK469)", J. Med. Chem., vol. 44, 2001, pp. 1758-1776.
Hazlet et al., "Bromination of 2-phenylphenyl acetate", STN Accession No. 1941:37645, Document No. 35:37645, Abstract of Journal of the American Chemical Society 63:1890-2 (1941).
Huston et al., "Chloro derivatives of o- and ρ-benzyl phenols. II. Some monochloro, dichloro and trichloro derivatives of ortho and para benzyl phenols", Journal of the American Chemical Society, vol. 55, No. 11, 1933, pp. 4639-4643.
Inukai et al., "ortho-Disubstituted F-benzenes. III. Preparation of (F-benzo)heterocyclic compounds from F-benzoic acid and F-phenol, and the reactions of some intermediary F-benzoyl- and F-phenoxy compounds", Bull. Chem. Soc. Jpn., vol. 54, No. 11, 1981, pp. 3447-3452.
Janczewski et al., "Effect of Molecular Structure on Optical Properties of Sulfoxide Systems. O-Phenoxyphenylsulfinylacetic Acid and some of Their Derivatives. Part II", Polish Journal of Chemistry, vol. 62, No. 1-3, 1964, pp. 91-105, XP008053171.
Kmonicek et al., "(Tert-Amino)-11-(4-Methylpiperazino)Dibenzo[b,f]Thiepins and their 10,11-Dihydro Derivatives; Synthesis and Neuroleptic Activity", *Collection Czechoslov. Chem. Commun.*, vol. 52, 1987, pp. 792-803, XP-002347166.

Lehmler et al., "Synthesis of hydroxylated PCB metabolites with the Suzuki-coupling", *Chemosphere*, vol. 45, 2001, pp. 1119-1127.

Litvak et al., "Synthesis and $S_NAr$ reactions of new dioxins and predioxins", *Chemosphere*, vol. 43, No. 4-7, 2001, pp. 493-495.

Lupus erythematosus [online], [retrieved Dec. 28, 2006]. Retrieved from the Internet, URL; http://en.wikipedia.org/wiki/Lupus_erythematosus>.

Ly et al., "Small-molecule CRTH2 antagonists for the treatment of allergic inflammation: an overview", *Expert Opin. Invest. Drugs* 14(7):769-773 (2005).

Maeda et al., "Studies on the Synthesis and Analgesic and Anti-inflammatory Activities of 2-Thiazolylamino- and 2-Thiazolyloxy-arylacetic Acid Derivatives", *Chem. Pharm. Bull.*, vol. 31, No. 10, 1983, pp. 3424-3445, XP-002347167.

Manoury et al., "Synthesis and Analgesic Activities of Some (4-Substituted phenyl-1-piperazinyl)alkyl 2-Aminobenzoates and 2-Aminonicotinates", Journal of Medicinal Chemistry, vol. 22(5), pp. 554-559 (1979).

Meunier et al., "Photochemical behaviour of dichlorprop [(±)-2-(2,4-dichlorophenoxy)propanoic acid] in aqueous solution", *Pest Management Science*, vol. 58, No. 8, 2002, pp. 845-852.

Morissette et al., "High-throughput crystallization: polymorphs, salts, co-crystals and solvates of pharmaceutical solids", *Advanced Drug Delivery Reviews* 56:275-300 (2004).

Moser et al., "Synthesis and Quantitative Structure-Activity Relationships of Diclofenac Analogues", *J. Med. Chem.*, vol. 33, 1990, pp. 2358-2368, XP-001024801.

Moshchitskii et al., "Smiles rearrangement of tetrachloropyridyl methyl-hydroxyphenyl sulfone", *Chemistry of Heterocyclic Compounds*, vol. 15, No. 7, 1979, pp. 1085-1088.

Ong et al., "Synthesis and Analgesic Activity of Some Spiro[dibenz[b,f]oxepin-10,4'-piperidine] Derivatives", *J. Med. Chem.*, vol. 22, No. 7, 1979, pp. 834-839, XP-002347163.

Rajsner et al., "Fluorinated tricyclic Neuroleptics: Synthesis and Pharmacology of 8-Fluoro-4-(4-Methylpiperazino)-4,5-Dihydrothieno[2,3-b]-1-Benzothiepin", *Collection Czechoslov. Chem. Commun.*, vol. 44, 1979, pp. 2997-3007, XP-002347164.

Selvi et al., "Vilsmeier cyclization of 2-amino phenoxyacetic acid", *Synthetic Communications*, vol. 31, No. 14, 2001, pp. 2199-2202.

Sindelar et al., "Synthesis of 3-Chloro-5-(4-Methylpiperazino)-6,7-Dihydro-5H-Dibenzo[b,g]Thiocin, An Eight-Membered Ring Homologue of the Neuroleptic Agent Octoclothepin", *Collection Czechoslov. Chem. Commun.*, vol. 45, 1980, pp. 491-503, XP-002347160.

Sindelar et al., "Fluorinated Tricyclic Neuroleptics with Prolonged Action: 3-Fluoro-8-Trifluoromethyl Derivatives of 10-(4-Methylpiperazino)- and 10-[4-(2-Hydroxyethyl)Piperazino]-10,11-Dihydrodibenzo-[b,f]Thiepin", *Collection Czechoslov. Chem. Commun.*, vol. 46, 1981, pp. 118-140, XP-002347168.

Sindler-Kulyk et al., "Synthesis of New 3-(Phenoxyphenyl)sydnones", *J. Hetercyclic Chem.*, vol. 29, No. 2, 1992, pp. 1013-1015, XP-002347161.

Stokker et al., "3-Hydroxy-3-methylglutaryl-coenzyme A Reductase Inhibitors. 5. 6-(Fluoren-9-yl)- and 6-(Fluoren-9-ylidenyl)-3,5-dihydroxyhexanoic Acids and Their Lactone Derivatives", *J. Med. Chem.* 29:852-855 (1986).

Thuillier, G., "Derives des acides 24 aryloxyacetiques a activite neurotrope", *Chimique Therapeutique*, vol. 1, No. 2, 1966, pp. 82-86.

Ulven et al., "Targeting of the Prostaglandin $D_2$ Receptors DP and CRTH2 for Treatment of Inflammation", *Current Topics in Medicinal Chemistry* 6:1427-1444 (2006).

Walsh et al., "Antiinflammatory Activity of N-(2-Benzoylphenyl)alanine Derivatives", *J. Med. Chem.*, vol. 27, 1984, pp. 1317-1321, XP-002347162.

Wheatley et al., "2-Benzylphenol Derivatives. III. Basic Ethers", *Journal of American Chemical Society*, vol. 71, No. 11, 1949, pp. 3795-3797.

Database CA [Online] Chemical Abstracts Service, Columbus, Ohio, US; XP002372494 retrieved from STN Database accession No. 1956:16264 abstract & Ott, Donald G. et al: "A carbon-14 tracer study of the alkaline rearrangement of chlorophenanthraquinones" Journal of the American Chemical Society, 77, 2325-9 CODEN:JACSAT; ISSN:0002-7863, 1955.

Database CAPLUS [Online] Chemical Abstracts Service, Columbus, Ohio, US; 1992, XP002372495 retrieved from STN Database accession No. 1992:255529 abstract & Ram, Bhagat et al: "Potential hypolipidemic agents part VI: synthesis and biological activity of some new 4-chloro/methyl-2-pyrazolylphenoxy alkanoates" Indian Drugs, vol. 29, No. 6, 1992, pp. 258-262.

Database WPI 1-3, 5, Section Ch, Week 200365 19, 20, Derwent Publications Ltd., London, GB, Class B03, AN 2003-689635 XP-002301315, WO03068744A1, Ishihara Sangyo Kaisha, Ltd., Aug. 21, 2003.

STN International, File CAPLUS, CAPLUS accession 1-10, No. 1987:597776, document No. 107:197776, Otsuka Pharmaceutical Factory, "Preparation of aminophenol derivatives as anticoagulants, analgesics, hypotensives, and diuretics", JP, A2, 62108859, May 20, 1987.

STN International, File CAPLUS, CAPLUS accession 1-5, 10, No. 1979:186607, document No. 90:186607, Ciba-Geigy, "Phenoxyphenoxyalkanecardoxylic acid derivatives", DE, Al, 2832435, Feb. 8, 1979.

STN International, File CAPLUS, CAPLUS accession 1-5, 10, No. 1971:53748, document No. 74:53748, Walker et al., "Synthesis of 5-phenyl-2,3,4,5-tetrahydro-1,4-benzoxazepines and corresponding 3-ones", & *Journal of Organic Chemistry* (1970), 36(2), 305-308.

STN International, File CAPLUS, CAPLUS accession 1-3, 5, 10, No. 1992:407796, document No. 117:7796, Tokuyama Soda Co., Ltd., "Preparation of thienyloxphenoxy group-containing carboxylic acids as microbicides", JP, A2, 04021677, Jan. 24, 1992.

STN International, File CAPLUS, CAPLUS accession 1-3, 5, 10, No. 1975:402045, document No. 83:2045, Shiley et al., "Fungicidal activity of some fluoroaromatic compounds", *Journal of Fluorine Chemistry* (1975), 5(4), 371-376.

STN International, File CAPLUS, CAPLUS accession 1, 3, 5, 10, No. 1972:405106, document No. 77:5106, Oniscu et al., "Monoethanolaminosulfonyl-,diethanolaminosulfonyl- and morpholinosulfonyl-phenoxyacetic derivatives", Buletinul Institutului Politehnic din Iasi, (1971), 14(3-4), 101-114.

STN International, File CAPLUS, CAPLUS accession 1, 3, 5, 10, No. 1961:22702, document No. 55:22702, Takano, K., "Condensation products of furfuryl alcohol. IV. Condensation products of furfuryl alcohol with cresols", Nippon Kagaku Zasshi (1959), 80, 678-681.

STN International, File CAPLUS, CAPLUS accession 1, 3-5, 10, No. 1958:25331, document No. 52:25331, Landa et al., "Properties of sulfide catalysts. V. Preparation of alkylphenols", Chemicke Listy pro Vedu a Prumysl (1957), 51, 1851-1857.

STN Intenational, File CAPLUS, CAPLUS accession 1, 3, 5, 10, No. 1971:498288, document No. 75:98288, Botez et al., "Phenoxybutyric acid sulfamides. I. Sulfamide derivatives of the α-phenoxy-, α-cresoxy-, and α-xylenoxybutyric acids", Buletinul Institutului Politehnic din Iasi (1970), 16(1-2), 161-172.

STN International, File CAPLUS, CAPLUS accession 1-7, 10, No. 1986:109631, document No. 104:109631, Yoshitomi Pharmaceutical Industries, Ltd., "Imidazole derivatives", JP, A2, 60142965, Jul. 29, 1985.

Inflammatory Bowel Disease [online] {retrieved on Apr. 7, 2008 from the internet} {URL:http://www.emedicinehealth.com/script/main/art.asp?articlekey=59121&pf=3&page=8}.

Rheumatoid arthritis [online] {retrieved on Apr. 7, 2008 from the internet} {URL:http://www.nlm.nih.gov/medlineplus/ency/article/000431.htm}.

Asthma [online] [retrieved on May 30, 2008] retrieved from the Internet URL:http://www.nlm.nih.gov/medlineplus/ency/article/000141.htm.

Rhinitis [online] retrieved on Nov. 12, 2008. Retrieved from URL; http://www.healthline.com/galecontent/rhinitis?print=true.

RN 110624-55-0, retrieved from CAPLUS; retrieved on Apr. 7, 2008.

USPTO Office Action in U.S. Appl. No. 10/552,082, mailed Oct. 29, 2007, 6 pages.

Fish & Richardson P.C., Amendment in Reply to Action of Oct. 29, 2007 in U.S. Appl. No. 10/552,082, filed Feb. 29, 2008, 18 pages.

USPTO Final Office Action in U.S. Appl. No. 10/552,082, mailed Jun. 9, 2008, 18 pages.
Fish & Richardson P.C., Amendment in Reply to Action of Jun. 9, 2008 in U.S. Appl. No. 10/552,082, filed Sep. 9, 2008, 11 pages.
USPTO Office Action in U.S. Appl. No. 10/552,082, mailed Dec. 4, 2008, 23 pages.
Fish & Richardson P.C., Amendment in Reply to Action of Dec. 4, 2008 in U.S. Appl. No. 10/552,082, filed Apr. 6, 2009, 8 pages.
USPTO Notice of Allowance in U.S. Appl. No. 10/552,082, mailed Jul. 1, 2009, 9 pages.
Fish & Richardson P.C., RCE and Interview Summary in response to Notice of Allowance of Jul. 1, 2009 in U.S. Appl. No. 10/552,082, filed Sep. 30, 2009, 2 pages.
USPTO Office Action in U.S. Appl. No. 10/552,082, mailed Jan. 7, 2010, 12 pages.
USPTO Office Action in U.S. Appl. No. 10/551,783, mailed Dec. 7, 2009, 15 pages.
USPTO Office Action in U.S. Appl. No. 10/569,065, mailed May 4, 2007, 12 pages.
Fish & Richardson P.C., Amendment in Reply to Action of May 4, 2007 in U.S. Appl. No. 10/569,065, filed Aug. 3, 2007, 14 pages.
USPTO Final Office Action in U.S. Appl. No. 10/569,065, mailed Oct. 17, 2007, 4 pages.
Fish & Richardson P.C., Amendment in Reply to Action of Oct. 17, 2007 in U.S. Appl. No. 10/569,065, filed Jan. 17, 2008, 9 pages.
USPTO Office Action in U.S. Appl. No. 10/569,065, mailed Apr. 16, 2008, 14 pages.
Fish & Richardson P.C., Amendment in Reply to Action of Apr. 16, 2008 in U.S. Appl. No. 10/569,065, filed Jul. 16, 2008, 38 pages.
USPTO Office Action in U.S. Appl. No. 10/569,065, mailed Oct. 28, 2008, 15 pages.
Fish & Richardson P.C., Amendment in Reply to Action of Oct. 28, 2008 in U.S. Appl. No. 10/569,065, filed Jan. 27, 2009, 7 pages.
USPTO Office Action in U.S. Appl. No. 10/569,065, mailed May 13, 2009, 10 pages.
Fish & Richardson P.C., Amendment in Reply to Action of May 13, 2009 in U.S. Appl. No. 10/569,065, filed Jul. 14, 2009, 9 pages.
USPTO Notice of Allowance in U.S. Appl. No. 10/569,065, mailed Oct. 23, 2009, 10 pages.
Fish & Richardson P.C., RCE and IDS in Reply to Notice of Allowance of Oct. 23, 2009 in U.S. Appl. No. 10/569,065, filed Nov. 5, 2009, 3 pages.
USPTO Office Action in U.S. Appl. No. 11/574,076, mailed Oct. 27, 2008, 23 pages.
Fish & Richardson P.C., Amendment in Reply to Action of Oct. 27, 2008 in U.S. Appl. No. 11/574,076, filed Apr. 27, 2009, 21 pages.
USPTO Final Office Action in U.S. Appl. No. 11/574,076, mailed Aug. 18, 2009, 7 pages.
Fish & Richardson P.C., RCE and Amendment in Reply to Action of Aug. 18, 2009 in U.S. Appl. No. 11/574,076, filed Dec. 18, 2009, 13 pages.
USPTO Office Action in U.S. Appl. No. 11/576,372, mailed Jul. 22, 2009, 19 pages.
Fish & Richardson P.C., Amendment in Reply to Action of Jul. 22, 2009 in U.S. Appl. No. 11/576,372, filed Jan. 22, 2010, 18 pages.
USPTO Office Action in U.S. Appl. No. 12/089,276, mailed Jun. 17, 2009, 28 pages.
Fish & Richardson P.C., Amendment in Reply to Action of Jun. 17, 2009 in U.S. Appl. No. 12/089,276, filed Sep. 22, 2009, 10 pages.
USPTO Notice of Allowance in U.S. Appl. No. 12/089,276, mailed Jan. 4, 2010, 6 pages.
USPTO Office Action in U.S. Appl. No. 12/092,431, mailed Aug. 4, 2009, 8 pages.
AstraZeneca AB: WO03066046 & WO03066047, "The use of indole-3-acetic acids as CRTH2 receptor antagonists", *Expert Opin. Ther. Patents* 14(1):125-128 (2004).
"DialogWeb Records", http://www.dialogweb.com/cgi/document?req=1284661379410, accessed Sep. 16, 2010.
Ebenezar et al., "Prostaglandins in the patent literature", *Expert Opin. Ther. Patents* 17(9):1131-1145 (2007).
Fromageot et al., "Photodecarboxylation of 2-(2'-carboxymethoxy-5'-methylphenyl)-benzotriazole", *Journal of Photochemistry and Photobiology, A: Chemistry* 44(1):93-98 (1988).

Manske et al., "Synthesis and Reactions of Some Dibenzoxepins", *Journal of American Chemical Society* 72:4797-4799 (1950).
Ram et al., "Potential Hypolipidemic Agents Part VI: Synthesis and Biological Activity of Some New 4-Chloro/Methyl-2-pyrazolylphenoxy Alkanoates", *Indian Drugs* 29(6), 258-262 (1992).
Ueda et al., "The Synthesis of 10-(4-Methylpiperazino)dibenzo[b,f] thiepin and Related Compounds. Neurotropic and Psychotropic Agents", *Chem. Pharm. Bull.* 23(10):2223-2231 (1975).
Wermuth, "Molecular Variations Based on Isosteric Replacements", The Practice of Medicinal Chemistry, 1996, chapter 13, pp. 203-237.
Preventing Asthma Symptoms [online] [retrieved on Apr. 23, 2010 from the internet] URL:http://www.webmd.com/asthma/guide/asthma-prevention.
Allergic Rhinitis—Prevention [online] [retrieved on Apr. 23, 2010 from the internet] URL:http://www.webmd.com/allergies/tc/allergic-rhinitis-prevention.
COPD Treatments: Improving Your Quality of Life [online] [retrieved on Apr. 23, 2010 from the internet] URL:http://www.webmd.com/lung/copd/copd-treatments-improving-your-quality-of-life.
Fish & Richardson P.C., Amendment in Reply to Action of Jan. 7, 2010 in U.S. Appl. No. 10/552,082, filed Jul. 2, 2010, 8 pages.
USPTO Notice of Allowance in U.S. Appl. No. 10/552,082, mailed Sep. 15, 2010, 12 pages.
Fish & Richardson P.C., Amendment in Reply to Action of Dec. 7, 2009 in U.S. Appl. No. 10/551,783, filed Mar. 8, 2010, 17 pages.
USPTO Office Action in U.S. Appl. No. 10/551,783, mailed Apr. 23, 2010, 9 pages.
Fish & Richardson P.C., Amendment in Reply to Action of Apr. 23, 2010 in U.S. Appl. No. 10/551,783, filed Jul. 2, 2010, 23 pages.
USPTO Office Action in U.S. Appl. No. 10/551,783, mailed Sep. 7, 2010, 6 pages.
USPTO Notice of Allowance in U.S. Appl. No. 10/569,065, mailed Jan. 28, 2010, 9 pages.
Fish & Richardson P.C., RCE and IDS in Reply to Notice of Allowance of Jan. 28, 2010 in U.S. Appl. No. 10/569,065, filed Mar. 31, 2010, 5 pages.
USPTO Notice of Allowance in U.S. Appl. No. 10/569,065, mailed May 13, 2010, 10 pages.
Fish & Richardson P.C., RCE and IDS in Reply to Notice of Allowance of May 13, 2010 in U.S. Appl. No. 10/569,065, filed Aug. 2, 2010, 4 pages.
USPTO Notice of Allowance in U.S. Appl. No. 10/569,065, mailed Sep. 1, 2010, 9 pages.
USPTO Office Action in U.S. Appl. No. 11/571,707, mailed Mar. 12, 2010, 16 pages.
Fish & Richardson P.C., Amendment in Reply to Action of Mar. 12, 2010 in U.S. Appl. No. 11/571,707, filed Sep. 3, 2010, 14 pages.
USPTO Notice of Allowance in U.S. Appl. No. 11/574,076, mailed Feb. 3, 2010, 12 pages.
Fish & Richardson P.C., Response to Notice of Allowance of Feb. 3, 2010 in U.S. Appl. No. 11/574,076, filed Apr. 30, 2010, 2 pages.
USPTO Final Office Action in U.S. Appl. No. 11/576,372, mailed May 7, 2010, 7 pages.
Fish & Richardson P.C., Reply to Action of May 7, 2010 in U.S. Appl. No. 11/576,372, filed Aug. 9, 2010, 10 pages.
USPTO Office Action in U.S. Appl. No. 11/576,372, mailed Sep. 2, 2010, 7 pages.
USPTO Office Action in U.S. Appl. No. 11/719,832, mailed Apr. 30, 2010, 20 pages.
Fish & Richardson P.C., Amendment in Reply to Action of Apr. 30, 2010 in U.S. Appl. No. 11/719,832, filed Aug. 30, 2010, 18 pages.
USPTO Office Action in U.S. Appl. No. 11/719,832, mailed Oct. 6, 2010, 12 pages.
Fish & Richardson P.C., RCE and IDS in Reply to Notice of Allowance of Jan. 4, 2010 in U.S. Appl. No. 12/089,276, filed Mar. 31, 2010, 7 pages.
USPTO Notice of Allowance in U.S. Appl. No. 12/089,276, mailed Apr. 21, 2010, 11 pages.
Fish & Richardson P.C., RCE and IDS in Reply to Notice of Allowance of Apr. 21, 2010 in U.S. Appl. No. 12/089,276, filed Jul. 21, 2010, 5 pages.

USPTO Notice of Allowance in U.S. Appl. No. 12/089,276, mailed Sep. 21, 2010, 9 pages.
Fish & Richardson P.C., Amendment in Reply to Action of Aug. 4, 2009 in U.S. Appl. No. 12/092,431, filed Feb. 3, 2010, 15 pages.
USPTO Final Office Action in U.S. Appl. No. 12/092,431, mailed May 4, 2010, 13 pages.
Fish & Richardson P.C., RCE, IDS and Amendment in Reply to Action of May 4, 2010 in U.S. Appl. No. 12/092,431, filed Sep. 7, 2010, 16 pages.

* cited by examiner

XRPD for Example 2 Polymorph A

XRPD for Example 4 Polymorph A

XRPD for Example 4 Polymorph B

BI-ARYL AMIDE COMPOUNDS AS CRTH2 RECEPTOR MODULATORS

This application claims the benefit under 35 U.S.C. §119(e) of application Ser. No. 60/948,012 (US) filed on 5 Jul. 2007, which is incorporated herein by reference in its entirety.

The present invention relates to certain phenoxyacetic acids and salts and solvates thereof useful as pharmaceutical compounds for treating respiratory disorders, pharmaceutical compositions containing them, and processes for their preparation. Crystalline forms are also disclosed.

WO2004/089885 and WO2006/021759 disclose a series of compounds which include amide based compounds which are active at the CRTh2 receptor and are expected to be useful for the treatment of various respiratory diseases, including asthma and COPD.

It has now been found that a bi-aryl amide not disclosed in the above applications is active at the CRTh2 receptor and shows particularly beneficial biological properties. The compound of the invention combines high CRTh2 potency with a usefully long half life and low metabolic turn over rate when measured in human hepatocytes.

In a first aspect the invention therefore provides a compound of formula (I):

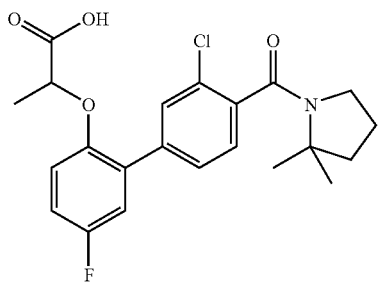

as a mixture of (2S)-2-({3'-chloro-4'-[(2,2-dimethylpyrrolidin-1-yl)carbonyl]-5-fluorobiphenyl-2-yl}oxy)propanoic acid and (2R)-2-({3'-chloro-4'-[(2,2-dimethylpyrrolidin-1-yl)carbonyl]-5-fluorobiphenyl-2-yl}oxy)propanoic acid, or solvates thereof or pharmaceutically acceptable salts thereof or solvates of pharmaceutically acceptable salts.

In an embodiment of the invention the compound (I) is substantially in the form of the (S) enantiomer. In one embodiment of the invention the compound (I) is present in at least 90% (S) enantiomer, in another embodiment at least 95% (S) enantiomer, and in another embodiment at least 99% (S) enantiomer.

A further embodiment of the invention therefore comprises a compound of formula (I):

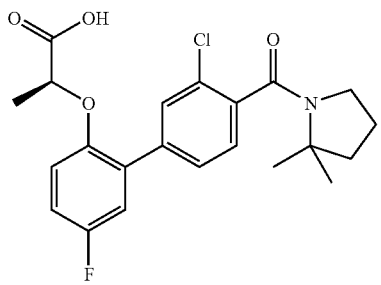

or a solvate thereof or pharmaceutically acceptable salt thereof or a solvate of a pharmaceutically acceptable salt.

As indicated above, the compound of formula (I) is capable of existing in other stereo isomeric forms. Other isomers including tautomers and mixtures thereof also form an aspect of the present invention. It will be understood that other isomers of the compounds of formula (I), specifically (2R)-2-({3'-chloro-4'-[(2,2-dimethylpyrrolidin-1-yl)carbonyl]-5-fluorobiphenyl-2-yl}oxy)propanoic acid will be expected to exhibit CRTh2 activity, as will mixtures of the (R) and (S) isomers.

The compound of formula (I) above may be converted to a solvate, pharmaceutically acceptable salt, or a solvate of a salt. In one embodiment of the invention the compound is in the form of a basic addition salt. Basic addition salts includes salts prepared from pharmaceutically acceptable non-toxic bases including inorganic and organic bases. Salts derived from inorganic bases include, but are not limited to aluminium, calcium, lithium, potassium, magnesium, sodium, zinc and other metal salts. Salts derived from pharmaceutically acceptable non-toxic bases include salts of primary, secondary or tertiary amines, substituted amines including naturally occurring substituted amines, cyclic amines and basic ion exchange resins, such as arginine, betaine, benzathine, caffeine, choline, chloroprocaine, cycloprocaine, N'N'-dibenzylethylenediamine, diethanolamine, diethylamine, 2-diethyl-aminoethanol, 2-dimethylaminoethanol, ethanolamine, ethylendiamine, N-ethyl-morpholine, N-ethyl piperidine, glucamine, glucosamine, histidine, hydrabamine, isopropylamine, lysine, meglumine, morpholine, piperazine, piperidine, polyamine resins, procaine, purines, tertiary butylamine (2-methylpropan-2-amine), theobromine, triethylamine, trimethylamine, tripropylamine, tromethamine, and the likethanolamine and the like, as well as non-toxic ammonium and quaternary ammonium, cations including, but not limited to, ammonium, tetramethylammonium, tetraethylammonium.

In one embodiment of the invention the compound of formula (I) is in the form of the 2-methylpropan-2-amine salt. Solvates, including hydrates, form a further aspect of the invention, as do solvates of salts, such as solvates of 2-methylpropan-2-amine salts.

The compounds of the invention can be prepared according to the procedures given in the examples below. Alternatively the compound can be prepared as a mixture of enantiomers which can then be separated and purified using techniques known in the art to give the pure or substantially pure (S) isomer, for example using chromatography. As a further alternative, isomers of intermediate compounds, such as compound (1f), can be separated prior to de-esterification. Intermediate compounds of formulae (1a), (1c), (1d) and (1f) as defined in the examples herein are novel and each form an embodiment of the invention. In a further aspect the invention provides a process for the preparation of a compound of formula (I) which comprises:

reaction of a compound of formula (1d):

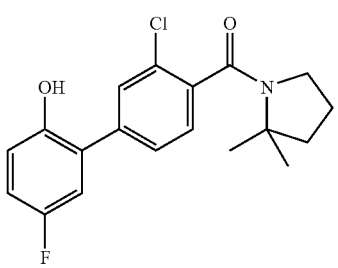

with a compound of formula (1e):

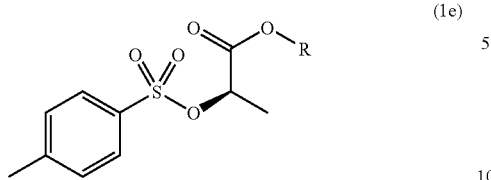

in which R is an ester forming group, followed by de-esterification of the resulting derivative and optionally forming a pharmaceutically acceptable salt, solvate or solvate of a salt. The ester forming group R is typically $C_{1-6}$alkyl, preferably methyl. The reaction is suitably carried out in a suitable solvent at elevated temperature, in one embodiment using the conditions specified in the examples herein.

Crystalline forms of compounds of formula (I) and salts/solvates thereof form a further aspect of the invention. One embodiment of the invention relates to crystalline forms of compounds of formula (I) in free acid form and as the the 2-methylpropan-2-amine salt as defined and exemplified herein.

The compound of the invention, or a pharmaceutically acceptable salt/solvate thereof, and crystalline forms as defined herein, can be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; anti-tussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;
2. bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;
3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);
4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis;cutaneous lymphomas, non-melanoma skin cancer and other dysplastic lesions; drug-induced disorders including fixed drug eruptions;
5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;
6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);
7. abdominal: hepatitis, including autoimmune, alcoholic and viral; fibrosis and cirrhosis of the liver; cholecystitis; pancreatitis, both acute and chronic;
8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);
9. allograft rejection: acute and chronic following, for example, transplantation of kidney, heart, liver, lung, bone marrow, skin or cornea or following blood transfusion; or chronic graft versus host disease;
10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

16. Diseases associated with raised levels of $PGD_2$ or its metabolites.

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CRTh2 receptor subfamily.

Particular conditions which can be treated with the compounds of the invention are asthma, rhinitis, COPD, and other diseases in which raised levels of $PGD_2$ or its metabolites. It is preferred that the compound of the invention are used to treat asthma, rhinitis or COPD.

In a further aspect, the present invention provides the use of a compound of formula (I), or a pharmaceutically acceptable salt or solvate thereof, as hereinbefore defined in the manufacture of a medicament for use in therapy.

In a further aspect, the present invention provides the use of a compound or formula (I), or a pharmaceutically acceptable salt or solvate thereof, as hereinbefore defined in the manufacture of a medicament for use in therapy in combination with drugs used to treat asthma, rhinitis or COPD (such as inhaled and oral steroids, inhaled β2-receptor agonists and oral leukotriene receptor antagonists).

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, with a monoclonal antibody targeting B-Lymphocytes (such as CD20 (rituximab), MRA-aIL16R and T-Lymphocytes, CTLA4-Ig, HuMax II-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY×1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY×7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenytoin, sodium valproate, amityptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-$B_1$- or $B_2$-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin $NK_1$ or $NK_3$ receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) inhibitor of P38; (xxiv) agent modulating the function of Toll-like receptors (TLR), (xxv) agent modulating the activity of purinergic receptors such as P2X7; or (xxvi) inhibitor of transcription factor activation such as NFkB, API, or STATS.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a famesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of CRTh2 receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating diseases mediated by PGD2 or its metabolites wherein the prostanoid binds to its receptor (especially CRTh2) receptor, which comprises administering to a patient a therapeutically effective amount of a compound of formula (I), or a pharmaceutically acceptable salt, solvate or prodrug thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

For the above-mentioned therapeutic uses the dosage administered will, of course, vary with the compound employed, the mode of administration, the treatment desired and the disorder indicated.

The compound of formula (I), prodrugs and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99%w (per cent by weight), more preferably from 0.05 to 80%w, still more preferably from 0.10 to 70%w, and even more preferably from 0.10 to 50%w, of active ingredient, all percentages by weight being based on total composition.

The present invention also provides a pharmaceutical composition comprising a compound of formula (I), or a pharmaceutically acceptable salt or solvate thereof, as herein before defined, in association with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compound of the invention is administered orally.

The invention will now be illustrated by the following non-limiting examples in which, unless stated otherwise:
(i) the title and sub-titled compounds of the examples and methods were named using the ACD labs/name program (version 8.0) from Advanced Chemical Development Inc, Canada;
(ii) unless stated otherwise, reverse phase preparative HPLC (RPHPLC) was conducted using a Symmetry, NovaPak or Ex-Terra reverse phase silica column;
(iii) flash column chromatography refers to normal phase silica chromatography;
(iv) solvents were dried with $MgSO_4$ or $Na_2SO_4$;
(v) Evaporations were carried out by rotary evaporation in vacuo and work-up procedures were carried out after removal of residual solids such as drying agents by filtration;
(vi) Unless otherwise stated, operations were carried out at ambient temperature, that is in the range 10-40° C. and under an atmosphere of an inert gas such as argon or nitrogen;
(vii) yields are given for illustration only and are not necessarily the maximum attainable;
(viii) the structures of the end-products of formula (I) were confirmed by nuclear (generally proton) magnetic resonance (NMR) and mass spectral techniques; peak multiplicities are shown as follows: s, singlet; d, doublet; t, triplet; m, multiplet; br, broad; q, quartet, quin, quintet. $^1H$ NMR data is quoted in the form of delta values for major diagnostic protons, given in parts per million (ppm) relative to tetramethylsilane (TMS) as an internal standard;
(ix) intermediates were characterised by thin layer chromatography (TLC), high-performance liquid chromatography (HPLC), mass spectrometry (MS), infra-red (IR) or NMR analysis;
(x) mass spectra (MS): generally only ions which indicate the parent mass are reported when given; MM=MultiMode;
(xi) the following abbreviations are used:
EtOAc Ethyl acetate
DMF N,N-Dimethyl formamide
NMP N-Methylpyrrolidinone
$MgSO_4$ Magnesium sulphate
THF Tetrahydrofuran
RT ROOM TEMPERATURE
DCM Dichloromethane
MeCN Acetonitrile

EXAMPLE 1

(2S)-2-({3'-chloro-4'-[(2,2-dimethylpyrrolidin-1-yl)carbonyl]-5-fluorobiphenyl-2-yl}oxy)propanoic acid a) 3-Chloro-5'-fluoro-2'-methoxybiphenyl-4-carboxylic acid

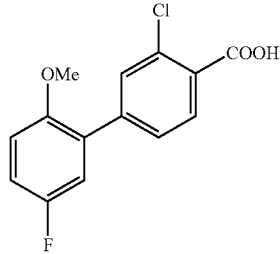 [SMILES: COc1ccc(F)cc1-c1ccc(C(=O)O)c(Cl)c1]

4-Bromo-2-chlorobenzoic acid (1.1 g) and 5-fluoro-2-methoxyphenylboronic acid (0.94 g) were suspended in toluene (20 mL) and ethanol (20 mL). Aqueous 2M sodium carbonate solution (16 mL) and tetrakis(triphenylphosphine)palladium(0) (0.14 g) were added and the reaction was heated at 95° C. for 20 h. The mixture was diluted with water, extracted with diethyl ether (discarded). The aqueous layer was acidified with aqueous 2M hydrochloric acid, extracted with ethyl acetate, dried ($MgSO_4$) and concentrated under reduced pressure to give the sub titled product as a cream solid (1.25 g).

MS: APCI(−ve) 279 b) 2,2-Dimethylpyrrolidine hydrochloride salt

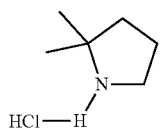

5,5-Dimethyl-1-pyrroline-N-oxide (2 g) in ethanol (40 mL) containing 10% Pd/C (0.5 g) was stirred under an atmosphere of hydrogen (4 bar) overnight. The mixture was flushed with nitrogen, filtered through Celite and the filtrate was treated with 4M HCl in dioxane (5 mL). The solution was concentrated under reduced pressure and azeotroped with toluene (×2) to give the sub titled product as an off-white solid (2.10 g).

1H NMR: δ (CDCl$_3$) 9.52 (2H, bs), 3.46-3.37 (2H, m), 2.15-2.01 (2H, m), 1.91-1.85 (2H, t), 1.55 (6H, s).

c) 1-[(3-Chloro-5'-fluoro-2'-methoxybiphenyl-4-yl)carbonyl]-2,2-dimethylpyrrolidine

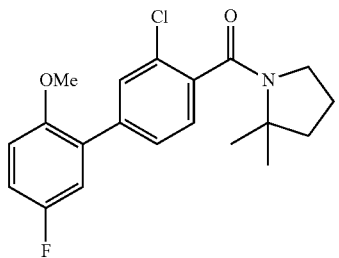 [SMILES: COc1ccc(F)cc1-c1ccc(C(=O)N2CCCC2(C)C)c(Cl)c1]

The product from step a) (1.25 g) in DCM (20 mL) was treated with oxalyl chloride (0.44 mL) and a drop of DMF. The mixture was stirred at rt for 1 h and concentrated under reduced pressure to give an oil which was azeotroped with toluene. This acid chloride was dissolved in DCM (10 mL) and treated with the product from b) (0.60 g) followed by triethylamine (0.4 mL) and the reaction was stirred at rt overnight. The organic layer was diluted with DCM and washed with water, dried (MgSO$_4$) and concentrated under reduced pressure to give the sub titled product as a cream solid (0.6 g).

MS: APCI(+ve) 362 d) 3'-Chloro-4'-[(2,2-dimethylpyrrolidin-1-yl)carbonyl]-5-fluorobiphenyl-2-ol

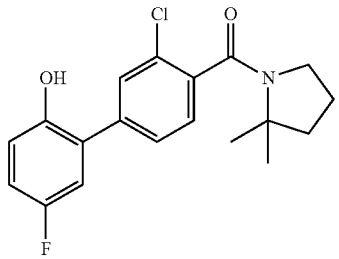 [SMILES: CC1(C)CCCN1C(=O)c1ccc(-c2cc(F)ccc2O)cc1Cl]

The product from step c) (0.6 g) in DCM (10 mL) was treated with 1.0 M boron tribromide in DCM (5 mL) and the reaction was stirred at rt overnight. The reaction was diluted with DCM and washed with ice water, dried (MgSO$_4$) and concentrated under reduced pressure to give the sub titled product as a solid (0.5 g).

MS: APCI(−ve) 346

1H NMR (300 MHz, D6-DMSO) δ 7.69 (1H, d), 7.59 (1H, dd), 7.34 (1H, d), 7.19 (1H, dd), 7.05 (1H, td), 6.95 (1H, dd), 3.17 (2H, t), 1.87-1.71 (4H, m), 1.52 (6H, s).

e) Methyl (2R)-2-{[(4-methylphenyl)sulfonyl]oxy}propanoate

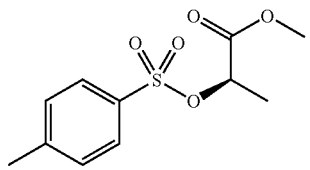

2-Hydroxy-propanoic acid methyl ester (6.66 g) was dissolved in MeCN (34 mL) and the solution cooled to 5° C. Triethylamine (9.8 mL) was added followed by trimethylamine hydrochloride (0.62 g). A solution of p-toluenesulfonyl chloride (11.6 g) in MeCN (34 mL) (sonicated to complete dissolution) was added over 20 min maintaining the temperature of the reaction below 5° C. The reaction was filtered through Celite and washed through with further MeCN. The filtrate was concentrated almost to dryness (bath 30° C.) and partitioned between diethyl ether and water. The organic layer was separated, dried (MgSO$_4$) and the solvents removed to give the sub titled product as a yellow oil that solidified in the freezer (13.71g).

1H NMR: δ (CDCl$_3$) 7.82 (2H, d), 7.35 (2H, d), 4.95 (1H, q), 3.67 (3H, s), 2.45 (3H, s), 1.51 (3H, d).

f) Methyl (2S)-2-({3'-chloro-4'-[(2,2-dimethylpyrrolidin-1-yl)carbonyl]-5-fluorobiphenyl-2-yl}oxy)propanoate

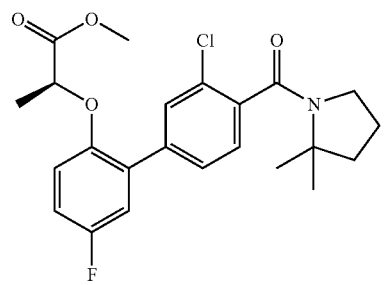 [SMILES: COC(=O)[C@H](C)Oc1ccc(F)cc1-c1ccc(C(=O)N2CCCC2(C)C)c(Cl)c1]

The intermediate from step d) (2.83 g) was dissolved in MeCN (30 mL). The product from step e) (2.11 g) and potassium carbonate (2.25 g) were added and the mixture was heated to 65° C. for 16 h. The mixture was cooled to rt and extracted with diethyl ether (×2), dried (MgSO$_4$) and concentrated under reduced pressure to give an oil. The oil was purified by flash column chromatography on silica using isohexane 3:1 ethyl acetate as eluent to give the sub titled product as a colourless oil (2.29 g).

MS: APCI(+ve) 434 g) (2S)-2-({3'-chloro-4'-[(2,2-dimethylpyrrolidin-1-yl)carbonyl]-5-fluorobiphenyl-2-yl}oxy)propanoic acid

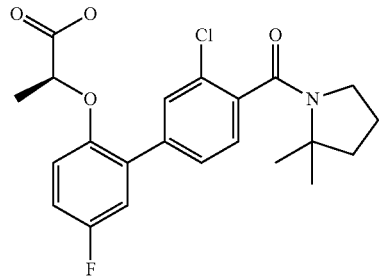 [SMILES: C[C@H](Oc1ccc(F)cc1-c1ccc(C(=O)N2CCCC2(C)C)c(Cl)c1)C(=O)O]

The product from step e) was treated with aqueous 2M sodium hydroxide solution (10 mL) and tetrahydrofuran (10 mL) and stirred for 1 h. The mixture was diluted with water, extracted with diethyl ether (discarded). The aqueous layer was acidified with 2M hydrochloric acid, extracted with ethyl acetate, dried (MgSO$_4$) and concentrated under reduced pressure to give an oil. The oil was purified by reverse phase prep HPLC (Xterra column using a gradient of 25-95% MeCN in 0.2% aqueous TFA as eluent) to give the title product a white solid (1.70 g).

MS: APCI (−ve) 418

1H NMR: δ(D6-DMSO) 7.81 (1H, s), 7.66-7.63 (1H, d), 7.42-7.14 (3H, m), 7.01-6.96 (1H, m), 4.93-4.86 (1H, q), 3.19-3.15 (2H, m), 1.86-1.73 (4H, m) 1.52 (6H, s), 1.45-1.42 (3H, d).

EXAMPLE 2

(2S)-2-({3'-chloro-4'-[(2,2-dimethylpyrrolidin-1-yl)carbonyl]-5-fluorobiphenyl-2-yl}oxy)propanoic acid 2-methylpropan-2-amine salt

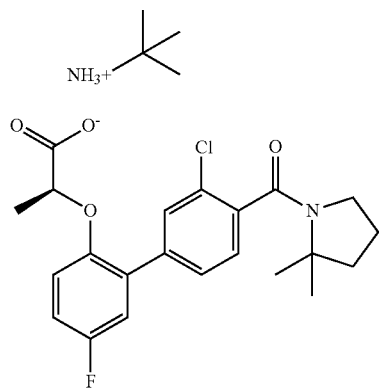

The product from example 1 step g) (1.20 g) was dissolved in ethyl acetate, tert-butylamine (1 eq) added and the volatiles removed in vacuo. The resulting solid was recrystallised from MeCN (30 mL) to give the title product as a crystaline white solid (0.51 g).

MS: APCI (−ve) 418

1H NMR: δ(D6-DMSO) 8.04 (1H, bm), 7.73 (1H, d), 7.32 (1H, d), 7.18 (1H, dd), 7.07 (1H, td), 6.88 (1H, dd), 4.42-4.40 (1H, q), 3.18 (2H, t), 1.84-1.75 (4H, m) 1.51 (6H, s), 1.33 (3H, d), 1.19 (9H, s).

EXAMPLE 3

Large Scale Synthesis (2S)-2-({3'-chloro-4'-[(2,2-dimethylpyrrolidin-1-yl)carbonyl]-5-fluorobiphenyl-2-yl}oxy)propanoic acid 2-methylpropan-2-amine salt a) 3-Chloro-5'-fluoro-2'-methoxybiphenyl-4-carboxylic acid

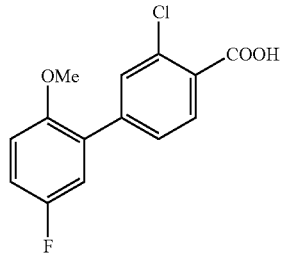 [SMILES: COc1ccc(F)cc1-c1ccc(C(=O)O)c(Cl)c1]

4-Bromo-2-chlorobenzoic acid (205 g) and 5-fluoro-2-methoxyphenylboronic acid (161 g) were dissolved in toluene (2 L) and ethanol (2 L) in a 10 L reactor vessel. Sodium carbonate (2 L of a 2 M aqueous solution) was added followed by tetrakis(triphenylphosphine)palladium(0) (15.39 g). The reaction was heated at 75° C. for 16 h. The reaction was diluted with water (2.5 L) and TBME (2 L) and stirred. Further water (0.5 L) was added and the mixture stirred for a further 5 min to complete dissolution of the solids. The aqueous layer was separated, filtered through a Celite pad and cooled to 15° C. The solution was acidified to pH 1 over 1 h by the addition of conc. HCl (532 mL, final pH1). The solid was filtered off and washed with ice cold water (400 ml) to give a tan solid. This was dried for 72 h in a vacuum oven at 45° C. over CaCl$_2$ to give the sub titled product (237 g).

MS: APCI (−ve) 279

$^1$H NMR: δ (D6-DMSO) 7.84 (d, 1H), 7.66 (d, 1H), 7.56 (dd, 1H), 7.21-7.30 (m, 2H), 7.14-7.18 (m, 1H), 3.78 (s, 3H).

This process was repeated on similar scale to give a further 228 g (465 g in total).

b) 2,2-Dimethylpyrrolidine

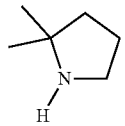

2,2-Dimethyl-3,4-dihydro-2H-pyrrole 1-oxide (0.31 L) was dissolved in EtOAc (3 L) and Pd/C (32 g) was added. The reaction was stirred under a hydrogen atmosphere (4 bar) for 16 h. The mixture was filtered through celite. Fresh Pd/C catalyst was added (32 g) and the hydrogenation continued for a further 24 h. The mixture was filtered through celite. Fresh Pd/C catalyst was added (32 g) and the hydrogenation continued for a further 24 h The mixture was filtered through celite. Fresh Pd/C catalyst was added (32 g) and the hydrogenation continued for a further 24 h. The mixture was filtered through celite. Fresh Pd/C catalyst was added (32 g) and the hydrogenation continued for a further 24 h. The mixture was filtered through celite. Fresh Pd/C catalyst was added (32 g) and the hydrogenation continued for a further 24 h. The mixture was filtered through celite to give a solution of the sub titled product in EtOAC (3.17 L) which was used without further manipulation.

Analysis of an aliquot by NMR showed the solution to have a concentration of 0.74 M.

GCMS confirmed the complete consumption of starting material.

GCMS MW 99 (100%)

1H NMR d (CDCL3) 2.90 (t, 2H), 1.74 (quintet, 2H), 1.46 (t, 2H), 1.09 (s, 6H).

c) 1-[(3-Chloro-5'-fluoro-2'-methoxybiphenyl-4-yl)carbonyl]-2,2-dimethylpyrrolidine

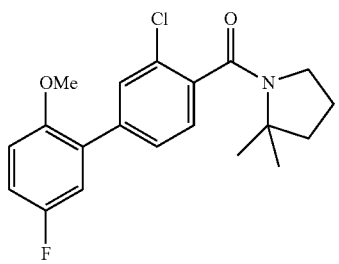 [SMILES: COc1ccc(F)cc1-c1ccc(C(=O)N2CCCC2(C)C)c(Cl)c1]

Thionyl chloride (0.177 L) was added to a suspension of the product from step a) (453 g) in toluene (4 L) and the reaction heated at 75° C. for 16 h. The volatiles were evaporated and the residue azeotroped with toluene (1 L) to give a beige solid. This was dissolved in ethyl acetate (1 L) and added dropwise over 30 min to a mixture of triethylamine (0.45 L) in ethyl acetate (0.5 L) and the product from step b) (2.62 L) at 10° C. The reaction temperature increased to 17° C. over the addition. The reaction was stirred at 23° C. for 1 h then washed with water (2 L), 1N HCl (2 L), sat. aqueous NaHCO$_3$ (2 L), and brine (2 L). The organic layer was separated, dried (Na$_2$SO$_4$) and solvent evaporated to give after drying the sub titled product as a colourless solid (550 g).

MS: APCI (+ve) 362/364 d) 3'-Chloro-4'-[(2,2-dimethylpyrrolidin-1-yl)carbonyl]-5-fluorobiphenyl-2-ol

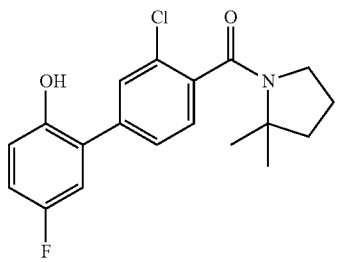 [SMILES: CC1(C)CCCN1C(=O)c1ccc(-c2cc(F)ccc2O)cc1Cl]

The product from c) (550 g) was suspended in 48% hydrobromic acid (4.5 L) and heated at 95° C. for 12 h then cooled to 23° C. and stirred for 72 h. The solid was filtered off and washed with water (4 L) and then dried to a constant weight to afford 527 g of solid. The solid was suspended in water (5 L) and stirred vigorously overnight. The solid was filtered off and washed with water until the filtrate was pH 7. The solid filter cake was washed with iso-hexane and dried in a vacuum oven at 45° C. for 72 h to give the sub titled product (496 g).

MS: APCI (+ve) 348

1H NMR δ (D6-DMSO) 9.77 (s, 1H), 7.69 (s, 1H), 7.59 (d, 1H), 7.35 (d, 1H), 7.19 (dd, 1H), 7.05 (td, 1H), 6.95 (dd, 1H), 3.17 (t, 2H), 1.75-1.85 (m, 4H), 1.52 (s, 6H).

e) Methyl (2S)-2-({3'-chloro-4'-[(2,2-dimethylpyrrolidin-1-yl)carbonyl]-5-fluorobiphenyl-2-yl}oxy)propanoate

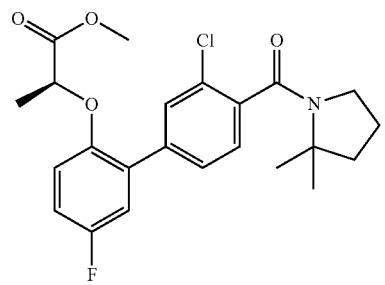 [SMILES: COC(=O)[C@H](C)Oc1ccc(F)cc1-c1ccc(C(=O)N2CCCC2(C)C)c(Cl)c1]

The product from step d) (206.4 g) was dissolved in NMP (1 L) and potassium tert-butoxide (65.9 g) added portionwise in (6×10 g and 1×5.9 g). The temperature rose to 35° C. during the addition. The reaction was stirred at RT for 30 min and then added dropwise over 3 h to a solution of methyl (2R)-2-{[(4-methylphenyl)sulfonyl]oxy}propanoate (example 1e, 169 g) in NMP (1 L) maintaining the temperature at 20° C. The reaction was split in half and each was independantly added to water (10 L) and extracted with diethyl ether (5 L). Each aqueous was salinified (add 1.5 Kg of NaCl) and the diethyl ether extraction repeated. The combined organics were dried (Na$_2$SO$_4$) and solvent evaporation gave the crude product (~300 g). This crude product was combined with an additional batch of crude product produced from a repeat synthesis (~310 g) and purified by large scale prep HPLC (Kromasil Silica 10 μm 60 Å, 25 cm×150 mm, 20% Ethyl acetate in iso-hexane, 100 ml/min. run time 20 min. 280 nm) to afford the title product (307 g)

MS: APCI (+ve) 434 f) (2S)-2-({3'-chloro-4'-[(2,2-dimethylpyrrolidin-1-yl)carbonyl]-5-fluorobiphenyl-2-yl}oxy)propanoic acid crystalline free acid

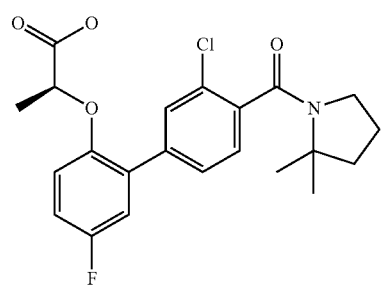 [SMILES: C[C@H](Oc1ccc(F)cc1-c1ccc(C(=O)N2CCCC2(C)C)c(Cl)c1)C(=O)O]

To a vigorously stirred slution of the product from step e) (307 g) in THF (3 L) was added a solution of lithium hydroxide (148 g) in water (0.6 L) and the reaction stirred at RT for 45 min. Aqueous 20% brine solution (2.5L) was added and the layers separated. The organic fraction was concentrated in vacuo, the residue re-dissolved in water (6 L) and the stirred mixture acidified to pH 1 with conc HCl. The resulting precipitate was filtered and washed with portions of water until the filtrate was pH 6. Iso-hexane was eluted through the filter cake to remove excess water and the solid was dried in a vacuum oven for 48 h at 40° C. to give the title product in crude form (259 g).

MS: APCI (+ve) 420

MeCN (1.3 L) was added and the mixture heated to 74.5° C. ( internal temperature) over 22 min until a clear solution was obtained. The mixture was maintained at this temperature for 10 min then cooled linearly to 20° C. over 1 h and then stirred for a further 1 h at 20° C. The resulting solid was filtered, washed with MeCN (250 mL) and iso-hexane (500 mL) and dried at 40° C. under vacuum for 72 h. to give the sub titled product (216 g).

MS: APCI (+ve) 420

1H NMR δ(D6-DMSO) 13.12 (s, 1H), 7.81 (s, 1H), 7.64 (d, 1H), 7.36 (d, 1H), 7.28 (dd, 1H), 7.18 (td, 1H), 6.99 (dd, 1H), 4.90 (q, 1H), 3.17 (t, 2H), 1.94-1.66 (m, 4H), 1.52 (s, 6H), 1.44 (d, 3H).

g) (2S)-2-({3'-chloro-4'-[(2,2-dimethylpyrrolidin-1-yl)carbonyl]-5-fluorobiphenyl-2-yl}oxy)propanoic acid 2-methylpropan-2-amine salt

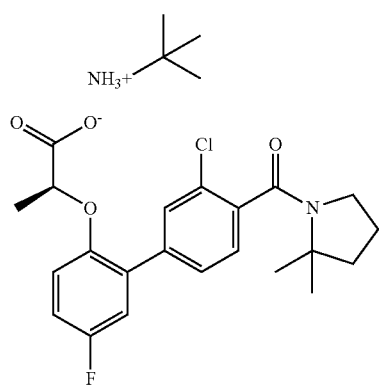

To a suspension of the free acid product from step f) (215.4 g) stirred in MeCN (1.5 L) at RT was added tert-butylamine (0.054 L) in MeCN (1 L) in one portion. The temperature rose from 23° C. to 28° C. An homogeneous solution was obtained momentarily before precipitation of a solid. The mixture was stirred for 1 h then combined with additional batches (36 g) of the title (tert-butylamine salt) product from example 2 and the mixture was stirred for 16 h. The solid was then filtered off, washed with ice-cold MeCN (500 mL) and dried to constant weight at 40° C. under vacuum to give the title product (280 g).

MS: APCI (+ve) 420

1H NMR δ (D6-DMSO) 8.17 (s, 2H), 8.06 (s, 1H), 7.73 (d, 1H), 7.32 (d, 1H), 7.18 (dd, 1H), 7.07 (td, 1H), 6.89 (dd, 1H), 4.44 (q, 1H), 3.18 (t, 2H), 1.89-1.69 (m, 4H), 1.49 (s, 6H), 1.33 (d, 3H), 1.18 (s, 9H).

EXAMPLE 4

(2S)-2-({3'-chloro-4'-[(2,2-dimethylpyrrolidin-1-yl)carbonyl]-5-fluorobiphenyl-2-yl}oxy)propanoic acid crystaline free acid

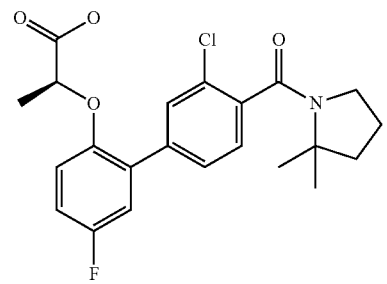 [SMILES: C[C@H](Oc1ccc(F)cc1-c1ccc(C(=O)N2CCCC2(C)C)c(Cl)c1)C(=O)O]

To a solution of the product from example 3 step e) (21.4 g) in THF (200 mL) was added a solution of lithium hydroxide (10.35 g) in water (40 mL) with vigorous stirring. After 45 min, aqueous 20% brine solution (160 mL) was added and the layers separated. The organic fraction was concentrated in vacuo, the residue re-dissolved in water (400 mL) and acidified to pH 2 with conc HCl whilst stirring. The resulting precipitate was filtered and washed with portions of water until the filtrate was pH 6. Iso-hexane was eluted through the filter cake to remove excess water and the solid was dried in a vacuum oven at 40° C. to give the title product in crude form (~20 g). A portion of this solid (1 g ) was recrystallised by heating to reflux in MeCN (5 mL) until dissolution, followed by cooling to RT, stirring for 16 h and collection of the resulting solid and drying in vacuo to afford the title product (0.759 g).

MS: APCI (+ve) 420

1H NMR δ (D6-DMSO) 13.13 (s, 1H), 7.81 (s, 1H), 7.64 (d, 1H), 7.36 (d, 1H), 7.28 (dd, 1H), 7.23-7.13 (m, 1H), 6.99 (dd, 1H), 4.90 (q, 1H), 3.17 (t, 2H), 1.89-1.70 (m, 4H), 1.52 (s, 6H), 1.44 (d, 3H).

Physical Form Data

INSTRUMENT DETAILS

Figure 1:
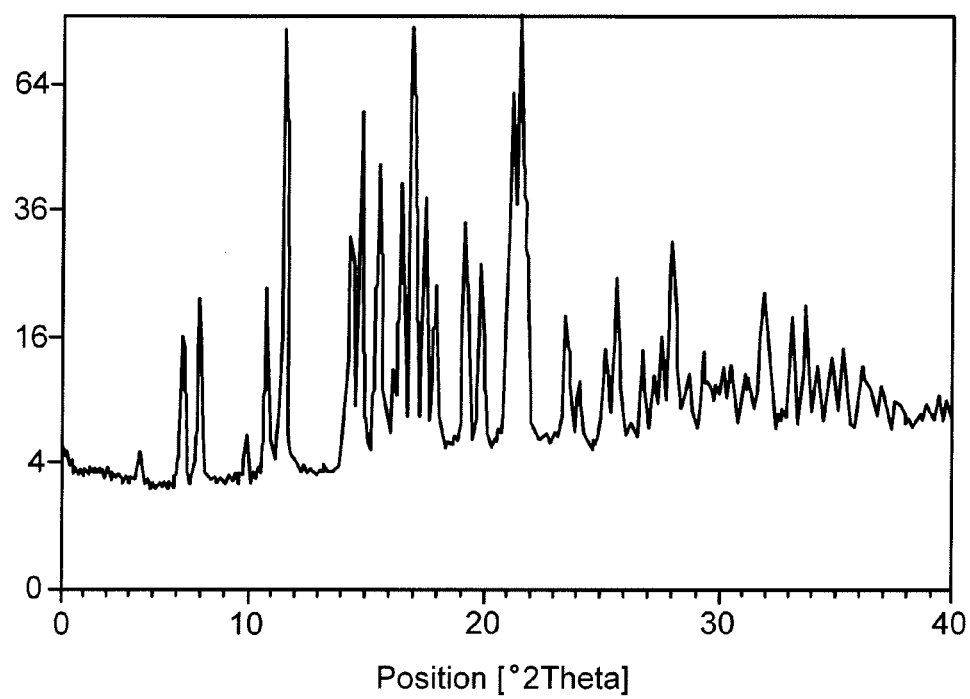
FIG. 1: X-ray powder diffraction pattern of polymorph A of Example 2 (2-methylpropan-2-amine salt)

XRPD data were collected using either a PANalytical CubiX PRO machine or a Philips X-Pert MPD machine.
XRPD—PANalytical CubiX PRO
  Data was collected with a PANalytical CubiX PRO machine in θ-θ configuration over the scan range 2° to 40° 2θ with 100-second exposure per 0.02° increment. The X-rays were generated by a copper long-fine focus tube operated at 45 kV and 40 mA. The wavelength of the copper X-rays was 1.5418 Å. The data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction.

Philips X-Pert MPD

Data was collected using a Philips X-Pert MPD machine in θ-θ and θ-2θ configurations over the scan range 2° to 40° 2θ with 100-second exposure per 0.03° increment. The X-rays were generated by a copper long-fine focus tube operated at 45 kV and 40 mA. The wavelengths of the copper X-rays were 1.5405 Å ($K_{\alpha1}$) and 1.5444 Å ($K_{\alpha2}$). The data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction.

DSC thermograms were measured using a TA Q1000 Differential Scanning Calorimeter, with aluminium pans and pierced lids. The sample weights varied between 0.5 to 5 mg. The procedure was carried out under a flow of nitrogen gas (50 ml/min) and the temperature studied from 25 to 300° C. at a constant rate of temperature increase of 10° C. per minute.

GVS profiles were measured using a Dynamic Vapour Sorption DVS-1 instrument. The solid sample ca. 1-5 mg was placed into a glass vessel and the weight of the sample was recorded during a dual cycle step method (40 to 90 to 0 to 90 to 0% relative humidity (RH), in steps of 10% RH).

Those skilled in the art will appreciate that 2-theta values may vary slightly depending on the instrument used and the precise nature of the experiment. The invention encompasses crystalline forms having 2-theta values substantially similar to those defined herein.

ANALYSIS OF EXAMPLE 2

(2S)-2-({3'-chloro-4'-[(2,2-dimethylpyrrolidin-1-yl)carbonyl]-5-fluorobiphenyl-2-yl}oxy)propanoic acid 2-methylpropan-2-amine salt polymorph A A sample of example 2 polymorph A was obtained by the procedure described in example 2 and was analysed by XRPD, DSC and GVS.

The melting temperature of example 2 polymorph A as determined by DSC occurred with onset of 157-165° C. with a water uptake of 0.6% between RH of 0% -80%, as measured by GVS. An XRPD diffraction pattern of example 2 polymorph A is presented in FIG. 1.

The polymorphic form produced from the large scale route (example 3 g) was identical to this example 2 polymorph A according to XRPD.

Slurry experiments in 10 solvents at room temperature for 7 days produced crystals of the previously determined polymorph A. Solvents investigated were: acetone, acetonitrile, dichloromethane, 1,4-dioxane, ethanol, ethyl acetate, n-heptane, cyclohexane, toluene and water.

ANALYSIS OF EXAMPLE 4

(2S)-2-({3'-chloro-4'-[(2,2-dimethylpyrrolidin-1-yl)carbonyl]-5-fluorobiphenyl-2-yl}oxy)propanoic acid free acid polymorph A A sample of example 4 polymorph A was obtained by the procedure described in example 4 and was analysed by XRPD, DSC and GVS.

The melting temperature of example 4 polymorph A as determined by DSC gave a single endothermic event, occurring at 180° C. (±2° C.), with a water uptake of 0.7% between RH of 0% -80%, as measured by GVS. An XRPD diffraction pattern of example 4 polymorph A is presented in FIG. 2.

The polymorphic form produced from the large scale route (example 3f) was identical to this example 4 polymorph A according to XRPD.

Slurry experiments in ethyl acetate, MeCN and n-heptane at RT and ethyl acetate at 50° C. for 9 days produced crystals of the previously determined polymorph A.

PREPARATION AND ANALYSIS OF EXAMPLE 4

(2S)-2-({3'-chloro-4'-[(2,2-dimethylpyrrolidin-1-yl)carbonyl]-5-fluorobiphenyl-2-yl}oxy)propanoic acid free acid polymorph B Slurry experiments with example 4 polymorph A in water at RT and water and MeCN at 50° C. for 9 days produced crystals of polymorph B. Polymorph B was also formed following slow evaporation of an ethanol slurry at RT.

The melting temperature of example 4 polymorph B as determined by DSC gave a single endothermic event, occurring at 188° C. (±2° C.).

Physical Form Data

FIG. 1 is an X-ray powder diffraction pattern of example 2, polymorph A.

Figure 2:
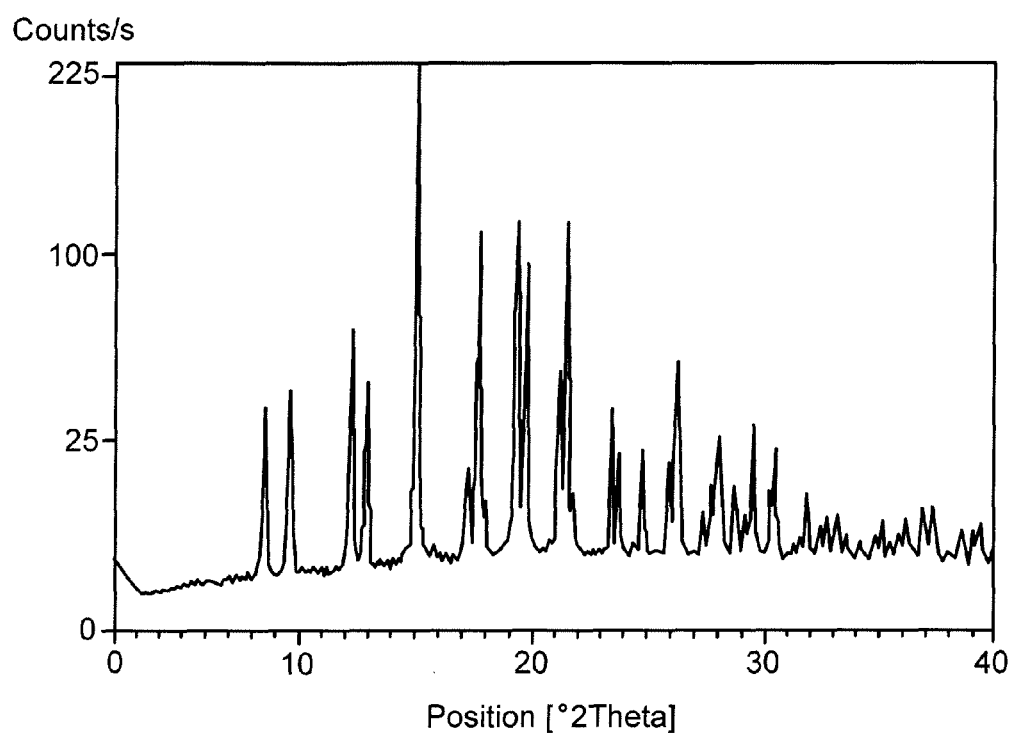
FIG. 2: X-ray powder diffraction pattern of polymorph A of Example 4 (free acid)

FIG. 2 is an X-ray powder diffraction pattern of example 4, polymorph A.

Figure 3:
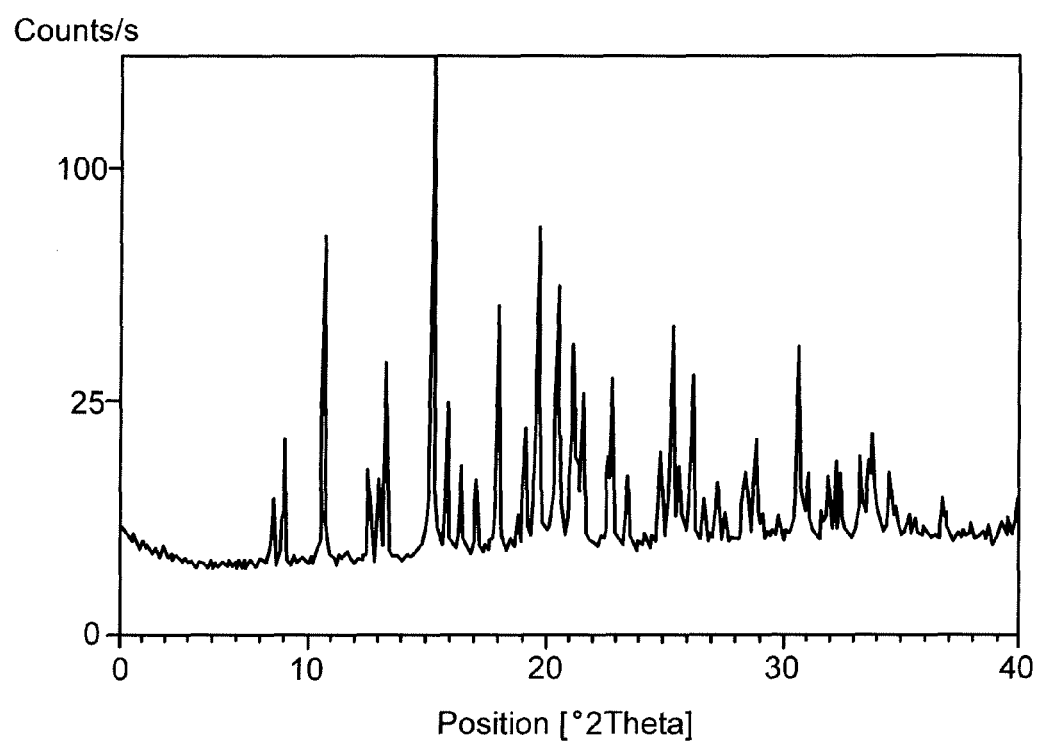
FIG. 3: X-ray powder diffraction pattern of polymorph B of Example 4 (free acid)

FIG. 3 is an X-ray powder diffraction pattern of example 4, polymorph B.

Pharmacological Data

Ligand Binding Assay

[$^3$H]PGD$_2$ was purchased from Perkin Elmer Life Sciences with a specific activity of 100-210 Ci/mmol. All other chemicals were of analytical grade.

HEK cells expressing rhCRTh2/Gα16 were routinely maintained in DMEM containing 10% Foetal Bovine Serum (HyClone), 1 mg/ml geneticin, 2 mM L-glutamine and 1% non-essential amino acids. For the preparation of membranes, the adherent transfected HEKcells were grown to confluence in two layer tissue culture factories (Fisher, catalogue number TKT-170-070E). Maximal levels of receptor expression were induced by addition of 500 mM sodium butyrate for the last 18 hours of culture. The adherent cells were washed once with phosphate buffered saline (PBS, 50 ml per cell factory) and detached by the addition of 50 ml per cell factory of ice-cold membrane homogenisation buffer [20 mM HEPES (pH 7.4), 01. mM dithiothreitol, 1 mM EDTA, 0.1 mM phenyl methyl sulphonyl fluoride and 100 μg/ml bacitracin]. Cells were pelleted by centrifugation at 220×g for 10 minutes at 4° C., re-suspended in half the original volume of fresh membrane homogenisation buffer and disrupted using a Polytron homogeniser for 2×20 second bursts keeping the tube in ice at all times. Unbroken cells were removed by centrifugation at 220×g for 10 minutes at 4° C. and the membrane fraction pelleted by centrifugation at 90000×g for 30 minutes at 4° C.

The final pellet was re-suspended in 4 ml of membrane homogenisation buffer per cell factory used and the protein content determined. Membranes were stored at −80° C. in suitable aliquots.

All assays were performed in Corning clear bottomed, white 96-well NBS plates (Fisher). Prior to assay, the HEK cell membranes containing CRTh2 were coated onto SPA PVT WGA beads (Amersham). For coating membranes were incubated with beads at typically 25 µg membrane protein per mg beads at 4° C. with constant agitation overnight. (The optimum coating concentrations were determined for each batch of membranes) The beads were pelleted by centrifugation (800×g for 7 minutes at 4° C.), washed once with assay buffer (50 mM HEPES pH 7.4 containing 5 mM magnesium chloride) and finally re-suspended in assay buffer at a bead concentration of 10 mg/ml.

Each assay contained 20 µl of 6.25 nM [$^3$H]PGD$_2$, 20 µl membrane saturated SPA beads both in assay buffer and 10 µl of compound solution or 13,14-dihydro-15-keto prostaglandin D$_2$ (DK-PGD$_2$, for determination of non-specific binding, Cayman chemical company).

Compounds and DK-PGD$_2$ were dissolved in DMSO and diluted in the same solvent to 100× the required final concentration. Assay buffer was added to give a final concentration of 10% DMSO (compounds were now at 10× the required final concentration) and this was the solution added to the assay plate. The assay plate was incubated at RT for 2 hours and counted on a Wallac Microbeta liquid scintillation counter (1 minute per well).

The compound of formula (I) has a pIC50 of 8.4.
Determination of Metabolic Intrinsic Clearance (CLint) Using Human Hepatocytes Compound stocks were prepared in dimethyl sulfoxide at 100-fold incubation concentration (100 µM). 10 µl of this 100 µM stock was added to a vial containing 490 µl of hepatocyte suspension buffer (without serum). A vial containing either human hepatocytes at a concentration of 2 million viable cells/ml was pre-incubated for 5 min in a shaking (80 oscillations/min) water bath at 37° C. along with the vial containing the drug/buffer mix.

Reactions were initiated by adding 500 µl of hepatocyte suspension to the 500 µl of drug/buffer mix (giving a final substrate concentration of 1 µM at 1% v/v dimethyl sulfoxide). Aliquots (40 µl) were removed at 5, 15, 30, 45, 60, 75 90 & 120 min and reactions were quenched in 80 µl of ice-cold methanol. Samples were subsequently frozen for 1 h at −20° C. and then centrifuged at 2000 g for 20 min at 4° C. The supernatants were removed and analysed by MS/MS and Clint was estimated from the slope of a natural Log of MS/MS response versus time plot. Using physiological scaling factors to account for hepatocellularity and liver weight in the human (Ito and Houston, 2004) hepatic blood clearance was predicted (Clh) using the method outlined by Riley et al., 2005. Typical acid drugs showing an intrinsic clearance value in this assay of <2 µl/min/e$^6$ cells show robust half lives in man consistent with a once-daily dose intervals. Example 1: Clint=<1 µl/min/e$^6$ (n=3).

The invention claimed is:

1. A mixture of (2S)-2-({3'-chloro-4'-[(2,2-dimethylpyrrolidin-1-yl)carbonyl]-5-fluorobiphenyl-2-yl}oxy)propanoic acid, or a pharmaceutically acceptable salt thereof; and (2R)-2-({3'-chloro-4'-[(2,2-dimethylpyrrolidin-1-yl)carbonyl]-5-fluorobiphenyl-2-yl}oxy)propanoic acid,-or a pharmaceutically acceptable salt thereof.

2. The mixture according to claim 1 in which (2S)-2-({3'-chloro-4'-[(2,2-dimethylpyrrolidin-1-yl)carbonyl]-5-fluorobiphenyl-2-yl)}oxy)propanoic acid is present in at least 95%.

3. The mixture according to claim 1 or 2 in which each of the (2S)-2-({3'-chloro-4'-[(2,2-dimethylpyrrolidin-1-yl)carbonyl]-5-fluorobiphenyl-2-yl}oxy)propanoic acid and (2R)-2-({3'-chloro-4'-[(2,2-dimethylpyn-1-yl)carbonyl]-5-fluoro-biphenyl-2-yl}oxy)propanoic acid is in the form of a 2-methylpropan-2-amine salt.

4. A compound of formula (I):

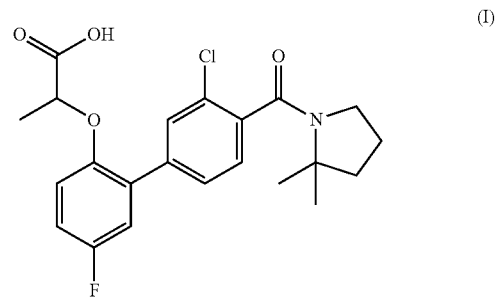 [SMILES: CC(Oc1ccc(F)cc1-c1ccc(C(=O)N2CCCC2(C)C)c(Cl)c1)C(=O)O]

or a pharmaceutically acceptable salt thereof.

5. An amine salt of a compound of formula (I) as claimed in claim 4.

6. The salt according to claim 5 which is (2S)-2-({3'-chloro-4'-[(2,2-dimethylpyrrolidin-1-yl)carbonyl]-5-fluoro-biphenyl-2-yl}oxy)propanoic acid 2-methylpropan-2-amine salt:

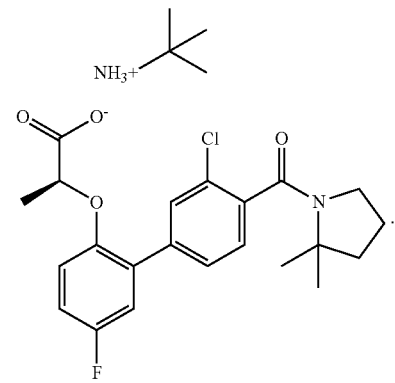

7. A crystalline form of the compound (2S)-2-({3'-chloro-4'-[(2,2-dimethylpyrrolidin-1-yl)carbonyl]-5-fluorobiphenyl-2-yl}oxy)propanoic acid 2-methylpropan-2-amine salt characterised by an X-ray powder diffraction pattern with peaks at at least one of the following 2-theta values measured using CuKα radiation: 14.6, 17.4 and 21.1.

8. A crystalline form of the compound (2S)-2-({3'-chloro-4'-[(2,2-dimethylpyrrolidin-1-yl)carbonyl]-5-fluorobiphenyl-2-yl}oxy)propanoic acid 2-methylpropan-2-amine salt characterised by an X-ray powder diffraction pattern substantially as shown in FIG. 1.

9. A crystalline form of the compound (2S)-2-({3'-chloro-4'-[(2,2-dimethylpyrrolidin-1-yl)carbonyl]-5-fluorobiphenyl-2-yl}oxy)propanoic acid characterised by an X-ray powder diffraction pattern with peaks at at least one of the following 2-theta values measured using CuKα radiation: 15.0, 19.2 and 21.4.

10. A crystalline form of the compound (2S)-2-({3'-chloro-4'-[(2,2-dimethylpyrrolidin-1-yl)carbonyl]-5-fluorobiphenyl-2-yl}oxy)propanoic acid characterised by an X-ray powder diffraction pattern substantially as shown in FIG. 2.

11. A crystalline form of the compound (2S)-2-({3'-chloro-4'-[(2,2-dimethylpyrrolidin-1-yl)carbonyl]-5-fluorobiphenyl-2-yl}oxy)propanoic acid characterised by an X-ray powder diffraction pattern with peaks at at least one of the following 2-theta values measured using CuKα radiation: 10.6, 13.2 and 15.1.

12. A crystalline form of the compound (2S)-2-({3'-chloro-4'-[(2,2-dimethylpyrrolidin-1-yl)carbonyl]-5-fluorobiphenyl-2-yl}oxy)propanoic acid characterised by an X-ray powder diffraction pattern substantially as shown in FIG. 3.

13. A compound of formula (1c):

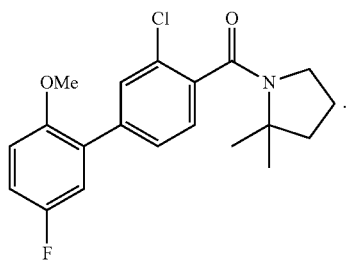 [SMILES: COc1ccc(F)cc1-c1ccc(C(=O)N2CCCC2(C)C)c(Cl)c1]

14. A compound of formula (1d):

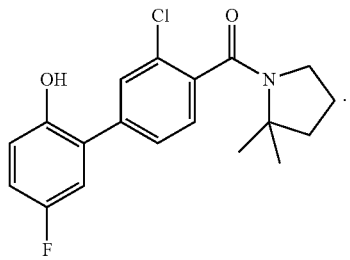 [SMILES: CC1(C)CCCN1C(=O)c1ccc(-c2cc(F)ccc2O)cc1Cl]

15. A compound of formula (1f):

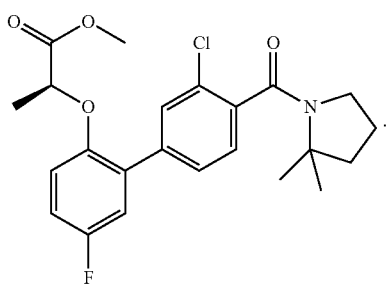 [SMILES: COC(=O)[C@H](C)Oc1ccc(F)cc1-c1ccc(C(=O)N2CCCC2(C)C)c(Cl)c1]

16. A pharmaceutical product comprising, in combination, a first active ingredient which is a mixture of (2S)-2-({3'-chloro-4'-[(2,2-dimethylpyrrolidin-1-yl)carbonyl]-5-fluorobiphenyl-2-yl}oxy)propanoic acid, or a pharmaceutically acceptable salt thereof; and (2R)-2-({3'-chloro-4'-[(2,2-dimethylpyrrolidin-1-yl)carbonyl]-5-fluorobiphenyl-2-yl}oxy)propanoic acid,-or a pharmaceutically acceptable salt thereof, and a second active ingredient which is selected from one or more of:

a PDE4 inhibitor;

a selective β2 adrenoceptor agonist;

a modulator of chemokine receptor function;

an inhibitor of p38 kinase function;

a glucocorticoid;

an anticholinergic agent and a non-steroidal glucocorticoid receptor antagonist.

17. A pharmaceutical product comprising, in combination, a first active ingredient which is

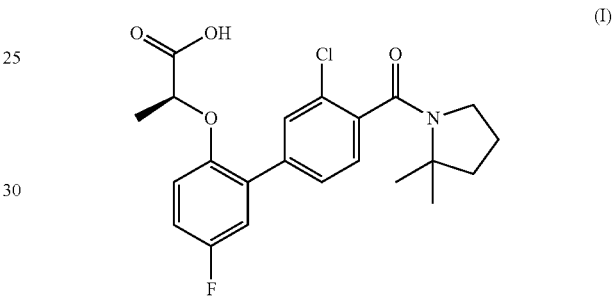

(I)

or a pharmaceutically acceptable salt thereof, and a second active ingredient which is selected from one or more of:

a PDE4 inhibitor;

a selective β2 adrenoceptor agonist;

a modulator of chemokine receptor function;

an inhibitor of p38 kinase function;

a glucocorticoid;

an anticholinergic agent and a non-steroidal glucocorticoid receptor antagonist.

* * * * *